United States Patent [19]

Sasson

[11] Patent Number: 5,132,475

[45] Date of Patent: Jul. 21, 1992

[54] QUATERNARY AMMONIUM FLUORIDE CATALYZED HALOGENATION OF CARBON ACIDS

[75] Inventor: Yoel Sasson, Jerusalem, Israel

[73] Assignee: E. I. Du Pont de Nemours and Company, Wilmington, Del.

[21] Appl. No.: 730,186

[22] Filed: Jul. 12, 1991

[51] Int. Cl.$^5$ .................. C07C 17/00; C07C 17/02; C07C 69/60; C07C 3/00

[52] U.S. Cl. .................. 570/200; 554/150; 558/460; 560/174; 564/204; 564/409; 568/316; 568/409; 568/437; 568/460; 570/101; 570/190; 570/206; 570/216

[58] Field of Search .................. 558/460; 560/174; 564/204, 209; 568/316, 409, 419, 436, 437, 459, 490, 495, 946, 460; 570/200, 216, 261, 101, 190; 260/408

[56] References Cited

U.S. PATENT DOCUMENTS 4,740,624  4/1988  Köhler et al. .................. 570/200
4,806,280  2/1989  Mignani et al. .................. 570/200

OTHER PUBLICATIONS

C. Y. Meyers et al., New Syntheses and Reactions of Organic Compounds: Reactions with Carbon Tetrachloride and Other Perhalomethanes in Powdered Potassium Hydroxide –t–Butyl Alcohol, pp. 197–278.
M. Mayosza et al., Rocz Chem. 43, pp. 671–676.
A. Jonczyk et al., J. Org. Chem., 44 pp. 1192–1194.
S. E. Lauritzen et al., Acta Chem. Scan., B35, 1981, pp. 263–268.
Y. Hori et al., Rikogakubu Shuho, 6, pp. 19–22.
Y. Hori et al., Chem. Lett., 1978, pp. 73–76.
W. P. Reeves et al., "The Phase Transfer Catalyzed Preparation of 2-Methyl-2-Trichbromethyl-3--Phenyloxirane" Synth Comm., 13 (11) 945-950 (1983).
C. Y. Meyers et al., "Facile and Selective Chlorination-Cleavage of Some Cyclanones and Cyclanols with the CCl$_4$-KOH-t-BuOH Reagent. In situ Conversion of Estrones and Estradiols into Dichlorodiosynolic Acids" J. Org. Chem., 43, 1985-1990.
C. R. Hauser et al., "Reactions of Alkali Diphenylmethides with Certain Polyhalides. Displacement on Halogen or Hydrogen", J. Org. Chem., 26 pp. 2627≧2629 (1961).

*Primary Examiner*—Werren B. Lone

[57] ABSTRACT

A process is disclosed for chlorinating, brominating and/or iodinating an organic substrate containing both a single acidic hydrogen atom and at least one electron withdrawing group attached to the same carbon atom. The process replaces the single acidic hydrogen with chlorine, bromine and/or iodine and involves reacting the substrate in solution with a halogenating agent (e.g., a perhalomethane wherein the halogen substituents are I, Br and/or Cl, a trihaloacetic acid ester wherein the halogen substituents are Br and/or Cl, or a perfluoroalkyl halide wherein the halide is I, Br and/or Cl) in the presence of a quaternary ammonium fluoride catalyst of the formula $R^1R^2R^3R^4NF$ where $R^1$, $R^2$, and $R^3$ and $R^4$ are independently chosen from the group consisting of hydrocarbyl radicals containing from 1 to about 20 carbon atoms.

21 Claims, No Drawings

QUATERNARY AMMONIUM FLUORIDE CATALYZED HALOGENATION OF CARBON ACIDS

FIELD OF THE INVENTION

This invention relates to the halogenation of compounds containing an acidic proton on a carbon atom, and more particularly providing catalysts for such halogenations.

BACKGROUND OF THE INVENTION

Under strongly basic conditions, tetrahalomethanes are known to generate chloronium or bromonium ions, which can be used to halogenate carbanions. The halogenation of ketones, sulfones, alcohols, and acidic hydrocarbons with perhalomethanes, e.g., $CCl_4$, $CBr_4$, $CBrCl_3$, $CCl_2Br_2$, in tert-butyl alcohol using powdered potassium hydroxide has been reviewed by C. Y. Meyers, et al., *Catalysis in Organic Synthesis* 1977, G. V. Smith, ed., pp. 197–278.

Halogenation reactions are also known to take place under conditions of phase transfer catalysis with a stoichiometric amount of aqueous sodium hydroxide as the base and benzyltriethylammonium chloride (TEBA) as catalyst (M. Majiszam et al., Rocz Chem. 1969, 43, 671–676; A. Jonczyk, et al., J. Org. Chem., 44, 1192–1194 (1979); S. E. Lauritzen, et al., Acta Chem. Scand. B 35, 1981, 263–268).

Active hydrogen compounds can also be chlorinated using 1,8-diazabicyclo[5.4.0]undecene-7 (i.e., "DBU") and $CCl_4$ (Y. Hori, et al., Rikogakubu Shuho (Saga Daigaku), 1978, 6, 19–22); and brominated using $DBU/BrCCl_3$ (Y. Hori, et al., Chem. Lett., 1978, 73–76).

U.S. Pat. No. 4,806,280, Mignani, et al., Rhone-Poulenc Sante (1989), discloses a process for preparing α-chlorinated unsaturated compounds with respect to two electron-attracting groups in the β-position. The preferred halogenating agents are molecular chlorine, sulfuryl chloride, N-chlorosuccinimide, and hexachloroethane.

SUMMARY OF THE INVENTION

This invention provides a process for halogenating an organic substrate containing both a single acidic proton and at least one electron withdrawing group attached to the same carbon atom, using a quaternary ammonium fluoride salt (e.g., tetra-n-butylammonium fluoride) as a catalyst, to replace the proton (i.e., the hydrogen atom) with a halogen atom selected from the group consisting of chlorine, bromine and iodine. The process is reversible and comprises the step of reacting the substrate in solution with a halogenating agent in the presence of a quaternary ammonium fluoride catalyst of the formula $R^1R^2R^3R^4NF$ where $R^1$, $R^2$, $R^3$ and $R^4$ are independently chosen from the group consisting of hydrocarbyl radicals containing from 1 to about 20 carbon atoms. Halogenating agents for this process include perhalomethanes wherein the halogen substituents are I, Br and/or Cl, trihaloacetic acid esters wherein the halogen substituents are Br and/or Cl, and perfluoroalkyl halides wherein the halide is I, Br and/or Cl.

It is an object of this invention to provide a process wherein the reaction takes place under conditions in which starting materials or products containing labile moieties such as ester groups and halogen groups, can be used or can be produced without being destroyed by hydrolytic processes that occur under strongly basic conditions.

It is another object of this invention to provide a process wherein exotic reagents, such as DBU, are not necessary.

Further objects, features and advantages of the invention will be apparent from the following detailed description.

DETAILED DESCRIPTION OF THE INVENTION

This invention provides a process of halogenating certain organic substrates by replacing an acidic hydrogen atom on a carbon atom with an atom of chlorine, bromine, or iodine. The process involves a liquid phase reaction of the substrate in solution using a halogenating agent and a catalytic amount of a quaternary ammonium fluoride salt.

The quaternary ammonium fluoride catalyst may be any compound of formula $R^1R^2R^3R^4NF$, where $R^1$, $R^2$, $R^3$, and $R^4$ are independently chosen from the group consisting of hydrocarbyl radicals containing from 1 to about 20 carbon atoms. $R^1$, $R^2$, $R^3$ and $R^4$ may be aliphatic (linear, branched or alicyclic), aromatic or mixed aliphatic-aromatic groups. Aliphatic groups containing from 1 to about 10 carbon atoms are preferred. Preferred aliphatic groups include alkyl groups such as n-butyl, n-hexyl, and n-octyl with n-butyl most preferred. Preferred aliphatic-aromatic groups contain from 7 to about 20 carbon atoms. For desirable reaction rates, the quaternary ammonium fluoride catalyst should generally be soluble in the reaction mixture. The quaternary ammonium fluoride is usually added at the start of the reaction along with the substrate and halogenating agent. However, the quaternary ammonium fluoride may also be formed in situ, for example, by reacting a metal fluoride of the formula MF, where M is K or Cs, and a quaternary ammonium salt of the formula $R^1R^2R^3R^4NJ$, where $R^1$, $R^2$, $R^3$, and $R^4$ are as defined above and J is an anion such as Cl, Br, I, or $HSO_4$. In situ formation of the quaternary ammonium fluoride typically produces a slower overall reaction rate.

Preferred catalysts include tetraethylammonium fluoride, tetra-n-butylammonium fluoride, tetra-n-hexylammonium fluoride, and tetra-n-octylammonium fluoride, with tetra-n-butylammonium fluoride being particularly preferred. Quaternary ammonium fluorides are relatively common, commercially available reagents, and are readily prepared by halogen exchange between metal fluoride salts and common quaternary ammonium compounds.

The substrate halogenated in the process of this invention must have a carbon atom bearing both a single acidic proton and at least one electron withdrawing group. Examples of substrates which can be halogenated in accordance with this invention include monosubstituted acetylene derivatives of the formula $R^5$—C≡C—H. $R^5$—C≡ is an electron withdrawing group. $R^5$ is a hydrocarbyl group, preferably containing between 1 and about 10 carbon atoms. $R^5$ may be an aliphatic (including linear, branched or alicyclic), aromatic or mixed aliphatic-aromatic group, and may be unsubstituted or substituted with a group inert under reaction conditions (e.g., a halogen). Examples of suitable aliphatic groups include linear or branched alkyl groups such as n-butyl, n-hexyl, n-octyl, isobutyl, and trifluoromethyl. Examples of suitable aromatic groups include —$C_6H_5$ and —$C_6H_4Br$. Examples of suitable aliphatic-aromatic groups include —$CH_2C_6H_5$. Substituted and unsubstituted aromatic groups (e.g., phenyl or substituted phenyl) are preferred.

Examples of substrates that can be halogenated in accordance with this invention also include compounds of the formula, HCXYZ, wherein X is an electron withdrawing group. The electron withdrawing group of X may be for example a nitrile group (i.e., —CN), an aldehyde group (i.e., —CHO), a ketone group of the formula —C(=O)—$R^6$, or an ester group of the formula —C(=O)—$OR^6$, where $R^6$ is a hydrocarbyl group, preferably containing between 1 and about 10 carbon atoms. $R^6$ may be an aliphatic (linear, branched or alicyclic) aromatic or mixed aliphatic-aromatic group and may be unsubstituted or substituted with a group which is inert under reaction conditions (e.g., a halogen). Examples of suitable X groups include —$COOCH_3$, —$COOC_2H_5$, —$COCH_3$ and —CN. Y may be selected from the same groups as X (i.e., it may be an electron withdrawing group) or it may be an aromatic group, preferably containing from 6 to about 20 carbon atoms (e.g., —$C_6H_5$) which is unsubstituted or substituted with a group which is inert under reaction conditions (e.g., a halogen). Examples of suitable Y groups include —$COOCH_3$, —$COOC_2H_5$, and —$COCH_3$. Z may be selected from the same groups as Y (i.e, it may be an electron withdrawing group or an unsubstituted or inert group-substituted aromatic group), or it may be an a linear or branched, saturated or unsaturated alkyl group, preferably containing between 1 and about 10 carbon atoms which is unsubstituted or substituted with a group which is inert under reaction conditions (e.g., a halogen). Examples of suitable Z groups include —$CH_3$, —$C_2H_5$ and —$C_6H_5$.

Examples of substrates that can be halogenated in accordance with this invention also include trihalomethanes wherein each of the three halogen groups is selected from the group consisting of Cl, Br, I and F. The three halogens of the trihalomethane function together as electron withdrawing groups such that the single hydrogen of the trihalomethane is acidic. Examples of trihalomethanes include $CHCl_3$, $CHBr_3$, $CHI_3$, $CHF_3$, $CHCl_2Br$, $CHCl_2I$, $CHCl_2F$, $CHBr_2Cl$, $CHBr_2I$ and $CHBr_2F$.

The substrate should be at least partially soluble in the reaction medium. The reaction medium should not interfere with the course of the reaction. The reaction medium can comprise, for example, toluene, tetrahydrofuran, or benzene. In many preferred embodiments, such as where the halogenating agent is a liquid at ambient temperature, the reaction medium consists essentially of the halogenating agent.

The halogenating agents used for this process are selected from the group consisting of perhalomethanes wherein the halogen substituents are I, Br and/or Cl (e.g., $CCl_4$, $CBr_4$, $CBrCl_3$ and/or $CCl_2Br_2$); trihaloacetic acid esters wherein the halogen substituents are Br and/or Cl (e.g., $Cl_3CC(=O)OCH_3$); and perfluoroalkyl halides, preferably containing from 1 to 10 carbon atoms wherein the halide is I, Br and/or Cl (e.g., perfluoro-n-hexyl iodide). The reaction is reversible and the halogenated substrate can itself serve as a donor for other halogenations (e.g., for halogenating bromoform). Accordingly, it is preferred to use a molar excess (e.g., at least about 10 percent excess) of halogenating agent (relative to the substrate).

A preferred halogenating agent for chlorination is $CCl_4$. A preferred halogenating agent for bromination is $CBrCl_3$. Preferred halogenating agents for iodination include perfluoroalkyl iodides. When the halogenating agent is not being used as the reaction medium, it is preferably soluble in the reaction medium.

The halogenation reaction can be run at a temperature of from about 0° C. to 100° C. The preferred temperature range is from about 10° to 50° C., and the most preferred range is from about 20° to 35° C.

One of the primary advantages of this process is that it need not be run under strongly alkaline conditions and does not require consumption of an equivalent of base, but only needs a catalytic amount of the quaternary ammonium fluoride salt. Thus the potential for hydrolysis of esters and other such materials that are labile in strong base, as well as hydrolysis of the halogenated product is reduced. However, in one of the preferred embodiments of this process, a mild inorganic base can be used to react with the trace amount of HCl, HBr, HI or HF sometimes generated by the reaction. These bases may be selected from among inorganic oxides, carbonates and fluorides that react with those hydrogen halides and are insoluble in the reaction medium. Preferred bases include $Na_2CO_3$, $K_2CO_3$, $Cs_2CO_3$ and KF. The use of these mild inorganic bases prolongs the useful life of the quaternary ammonium fluoride catalysts.

The time of reaction typically ranges from about 30 seconds to about 24 hours and depends upon such factors as the nature and concentration of the reactants and the catalyst.

One method of practicing this invention involves stirring the substrate and halogenating agent at about room temperature (i.e., about 24° C.) with sufficient catalyst to achieve halogenation within about 15 min. Preferably smaller amounts of catalyst are used and the substrate, halogenating agent and catalyst are stirred together with sufficient solid potassium carbonate at about room temperature (i.e., about 24° C.) to achieve halogenation within about 5 hours.

Practice of the invention will become further apparent from the following non-limiting examples.

EXAMPLE 1

In a 10 mL round-bottom flask, a mixture of 1.46 g dimethyl methylmalonate (10 mmol), 1.69 g tetrachloromethane (11 mmol), and 63 mg tetra-n-butylammonium fluoride (0.2 mmol) was mixed by a magnetic stirrer for 15 min at 24° C. Gas chromatographic analysis of the product mixture showed that the solution contained 1.14 g of dimethyl α-chloro-α-methylmalonate (63% yield).

EXAMPLE 2

In a 10 mL round-bottom flask, a mixture of 1.46 g dimethyl methylmalonate (10 mmol), 1.69 g tetrachloromethane (11 mmol), 0.27 g potassium carbonate (2 mmol), and 63 mg tetra-n-butylammonium fluoride (0.2 mmol) was mixed by a magnetic stirrer at 24° C. for 5 h. The product mixture was filtered, and gas chromatographic analysis of the filtrate showed the presence of 1.8 g of dimethyl α-chloro-α-methylmalonate (99% yield).

EXAMPLE 3

In a 10 mL round-bottom flask, a mixture of 0.51 g phenylacetylene (5 mmol), 0.7 g potassium carbonate (5 mmol), 165 mg tetra-n-butylammonium fluoride trihydrate, and 3 mL tetrachloromethane was stirred at 24° C. for 10 min. After filtration of the solids, the filtrate was found to contain 0.68 g of 1-chloro-2-phenylacetylene (99% yield).

EXAMPLE 4

In a 10 mL round-bottom flask, 1.88 g of diethyl ethylmalonate (10 mmol), 2.18 g of bromotrichloromethane (11 mmol), 79 mg of tetra-n-butylammonium fluoride trihydrate (0.25 mmol), and 69 mg of potassium carbonate (0.5 mmol) were stirred at 24° C. for 1 h. An exothermic reaction caused the temperature of the mixture to rise to 40° C. After filtration of the solids, the solution was found to contain 2.5 g (95% yield) of diethyl α-bromo-α-ethylmalonate.

EXAMPLE 5

In a 10 mL round-bottom flask, 1.88 g of diethyl ethylmalonate (10 mmol), 2.10 g of ethyl trichloroacetate (11 mmol), 158 mg of tetra-n-butylammonium fluoride trihydrate (0.5 mmol), and 69 mg of potassium carbonate (0.5 mmol) were stirred at 24° C. for 5 h. After filtration, the solution was found to contain 1.56 g (70% yield) of diethyl α-chloro-α-ethylmalonate.

EXAMPLE 6

In a 10 mL round-bottom flask, 1.02 g of phenylacetylene (10 mmol), 2.1 g bromotrichloromethane (10.5 mmol) and 100 mg of tetra-n-butylammonium fluoride trihydrate (0.316 mmol) were stirred at 24° C. for 15 min. The temperature of the mixture rose to 33° C. in the course of the process. Analysis of the resulting mixture showed that it contained 1.72 g of 1-bromo-2-phenylacetylene (95% yield) and 0.05 g of the unconverted phenylacetylene.

EXAMPLE 7

In a 10 mL round-bottom flask, 1.02 g of phenylacetylene (10 mmol), 4.46 g of perfluoro-n-hexyl iodide (10 mmol), and 300 mg of tetra-n-butylammonium fluoride trihydrate (0.948 mmol) were mixed at 24° C. for 1 h. Gas chromatographic analysis of the resulting mixture showed that it contained 1.26 g of 1-iodo-2phenylacetylene (55% yield) and 0.45 g of unconverted phenylacetylene.

EXAMPLE 8

In a 10 mL round-bottom flask, 1.58 g of ethyl 2-acetylbutyrate (10 mmol), 2.1 g bromotrichloromethane (10.5 mmol), and 200 mg of tetra-n-butylammonium fluoride trihydrate (0.632 mmol) were mixed at 24° C. for 1 h. Gas chromatographic analysis of the resulting mixture showed the presence of 1.34 g of ethyl 2-acetyl-2-bromobutyrate (56% yield).

EXAMPLE 9

A solution of 3.25 g tetrabromomethane (10 mmol), 1.46 g dimethyl methylmalonate (10 mmol), and 100 mg tetra-n-butylammonium fluoride trihydrate (0.316 mmol) in 5 mL tetrahydrofuran (THF) was stirred for 10 min at 24° C. Gas chromatographic analysis of the resulting mixture showed that it contained 87% yield of both dimethyl α-bromo-α-methylmalonate (1.97 g) and bromoform (2.2 g).

EXAMPLE 10

Bromoform (1.01 g, 0.4 mol), 1.46 g dimethyl methylmalonate, 200 mg tetra-n-butylammonium fluoride trihydrate (0.632 mmol), and 5 mL carbon tetrachloride were mixed at 24° C. for 2 h. The solution was found to contain 2.01 g (89% yield) of dimethyl α-bromo-α-methylmalonate.

Particular embodiments of the invention are included in the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for halogenating an organic carbon acid compound containing both a single acidic hydrogen atom and at least one electron withdrawing group attached to the same carbon atom, comprising the step of: reacting said carbon acid compound in solution with a halogenating agent selected from the group consisting of perhalomethanes wherein the halogen substituents are I, Br, Cl or mixtures thereof, trihaloacetic acid esters wherein the halogen substituents are Br, Cl or mixtures thereof, and perfluoroalkyl halides wherein the halide is I, Br, Cl or mixtures thereof, in the presence of a quaternary ammonium fluoride catalyst of the formula $R^1R^2R^3R^4NF$ where $R^1$, $R^2$, $R^3$ and $R^4$ are independently chosen from the group consisting of hydrocarbyl radicals containing from 1 to about 20 carbon atoms, to provide a halogenated product wherein said single acidic hydrogen atom of the carbon acid compound is replaced with a halogen selected from the group consisting of chlorine, bromine and iodine.

2. The process of claim 1 wherein the halogenation reaction is run at a temperature between 0° and 100° C.

3. The process of claim 2 wherein the carbon acid compound is a compound of the formula $R^5$—C≡C—H wherein $R^5$ is a hydrocarbyl group containing between 1 and about 10 carbon atoms.

4. The process of claim 3 wherein the carbon acid compound is phenylacetylene.

5. The process of claim 2 wherein the carbon acid compound is a compound of the formula HCXYZ wherein X is an electron withdrawing group, Y is an electron withdrawing group or an aromatic group which is unsubstituted or substituted with a group which is inert under reaction conditions, and Z is an electron withdrawing group, an aromatic group which is unsubstituted or substituted with a group which is inert under reaction conditions, or a linear or branched, saturated or unsaturated alkyl group which is unsubstituted or substituted with a group which is inert under reaction conditions.

6. The process of claim 5 wherein the electron withdrawing group is a nitrile, an aldehyde group, a ketone group of the formula —C(=O)—$R^6$ or an ester group of the formula —C(=O)—O$R^6$ where $R^6$ is a hydrocarbyl group.

7. The process of claim 5 wherein X is —COOCH$_3$, —COOC$_2$H$_5$, —COCH$_3$ or —CN; wherein Y is —COOCH$_3$, —COOC$_2$H$_5$ or —COCH$_3$; and wherein Z is —CH$_3$, —C$_2$H$_5$ or —C$_6$H$_5$.

8. The process of claim 2 wherein the carbon acid compound is a trihalomethane.

9. The process of claim 2 wherein the halogenating agent is a perhalomethane.

10. The process of claim 9 wherein the carbon acid compound is chlorinated and the halogenating agent is $CCl_4$.

11. The process of claim 9 wherein the carbon acid compound is brominated and the halogenating agent is $CBrCl_3$.

12. The process of claim 2 wherein the halogenating agent is a trihaloacetic acid.

13. The process of claim 2 wherein the halogenating agent is a perfluoroalkyl halide.

14. The process of claim 13 wherein the carbon acid compound is iodinated and the halogenating agent is perfluoro-n-hexyl iodide.

15. The process of claim 2 wherein the reaction medium consists essentially of the halogenating agent.

16. The process of claim 2 wherein a mild inorganic base is used which is insoluble in the reaction medium and reacts with hydrogen halides.

17. The process of claim 16 wherein the inorganic base is selected from $Na_2CO_3$, $K_2CO_3$, $Cs_2CO_3$ and KF.

18. The process of claim 2 wherein $R^1$, $R^2$, $R^3$ and $R^4$ are aliphatic groups containing from 1 to about 10 carbon atoms.

19. The process of claim 2 wherein $R^1$, $R^2$, $R^3$ and $R^4$ are alkyl groups.

20. The process of claim 2 wherein $R^1$, $R^2$, $R^3$ and $R^4$ are selected from n-butyl, n-hexyl and n-octyl.

21. The process of claim 2 wherein $R^1$, $R^2$, $R^3$ and $R^4$ are n-butyl.

* * * * *